(12) United States Patent
Dodge, II et al.

(10) Patent No.: US 6,689,934 B2
(45) Date of Patent: Feb. 10, 2004

(54) ABSORBENT MATERIALS HAVING IMPROVED FLUID INTAKE AND LOCK-UP PROPERTIES

(75) Inventors: Richard Norris Dodge, II, Appleton, WI (US); Nancy Birbiglia Lange, Oshkosh, WI (US); Jayant Chakravarty, Appleton, WI (US); Jian Qin, Appleton, WI (US); Sridhar Ranganathan, Suwanee, GA (US); Fu-Jya Daniel Tsai, Appleton, WI (US); Cathleen M. Uttecht, Menasha, WI (US); Xiaomin Zhang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/291,239

(22) Filed: Nov. 8, 2002

(65) Prior Publication Data

US 2003/0130640 A1 Jul. 10, 2003

Related U.S. Application Data

(63) Continuation-in-part of application No. 10/017,683, filed on Dec. 14, 2001.

(51) Int. Cl.[7] ................................................. A61F 13/15
(52) U.S. Cl. ....................................................... 604/367
(58) Field of Search .................................. 604/367–377

(56) References Cited

U.S. PATENT DOCUMENTS

| 4,127,547 A | 11/1978 | Smarook |
| 4,179,540 A | 12/1979 | Smarook |
| 4,394,930 A | 7/1983 | Korpman |
| 4,410,571 A | 10/1983 | Korpman |
| 4,559,243 A | 12/1985 | Pässler et al. |
| 4,758,466 A | 7/1988 | Dabi et al. |
| 5,147,343 A | * 9/1992 | Kellenberger ............... 604/368 |
| 5,149,335 A | 9/1992 | Kellenberger et al. |
| 5,252,619 A | 10/1993 | Brownscombe et al. |
| 5,268,224 A | 12/1993 | DesMarais et al. |

(List continued on next page.)

FOREIGN PATENT DOCUMENTS

| WO | 86/03505 | 6/1986 |
| WO | 99/61518 | 12/1999 |
| WO | 00/38610 | 7/2000 |
| WO | 00/78369 | 12/2000 |
| WO | 01/13843 | 3/2001 |
| WO | 02/49565 | 6/2002 |

Primary Examiner—Weilun Lo
Assistant Examiner—Michele Kidwell
(74) Attorney, Agent, or Firm—Pauley Petersen & Erickson

(57) ABSTRACT

Disclosed are absorbent composites, useful in an absorbent article, having high liquid intake rates. The absorbent composites may also have a rapid liquid lock-up. Absorbent composites of this invention have an intake rate of at least about 1.9 cc liquid/second at an 80% absorbent composite saturation level and a liquid lock-up fraction of at least about 0.70 at 50% superabsorbent material saturation. The absorbent composites of this invention can be a freeze-dried composite, an airformed absorbent composite, or other fibrous or non-fibrous absorbent composites.

24 Claims, 8 Drawing Sheets

U.S. PATENT DOCUMENTS

| | | |
|---|---|---|
| 5,290,820 A | 3/1994 | Brownscombe et al. |
| 5,300,054 A | 4/1994 | Feist et al. |
| 5,304,161 A | 4/1994 | Noel et al. |
| 5,328,935 A | 7/1994 | Van Phan et al. |
| 5,334,621 A | 8/1994 | Beshouri |
| 5,338,766 A | 8/1994 | Phan et al. |
| 5,358,974 A | 10/1994 | Brownscombe et al. |
| 5,364,382 A | 11/1994 | Latimer et al. |
| 5,372,877 A | 12/1994 | Kannankeril |
| 5,439,458 A | 8/1995 | Noel et al. |
| 5,490,846 A | 2/1996 | Ellis et al. |
| 5,509,915 A | 4/1996 | Hanson et al. |
| 5,550,167 A | 8/1996 | DesMarais |
| 5,563,179 A | 10/1996 | Stone et al. |
| 5,571,849 A | 11/1996 | DesMarais |
| 5,573,994 A | 11/1996 | Kabra et al. |
| 5,601,542 A | 2/1997 | Melius et al. |
| 5,612,385 A | 3/1997 | Ceaser et al. |
| 5,632,737 A | 5/1997 | Stone et al. |
| 5,651,862 A | 7/1997 | Anderson et al. |
| 5,692,939 A | 12/1997 | DesMarais |
| 5,733,272 A | 3/1998 | Brunner et al. |
| 5,763,067 A | 6/1998 | Brüggemann et al. |
| 5,763,499 A | 6/1998 | DesMarais |
| 5,786,395 A | 7/1998 | Stone et al. |
| 5,795,921 A | 8/1998 | Dyer et al. |
| 5,843,063 A | 12/1998 | Anderson et al. |
| 5,849,805 A | 12/1998 | Dyer |
| 5,851,648 A | 12/1998 | Stone et al. |
| 5,851,672 A | 12/1998 | Wang et al. |
| 5,869,171 A | 2/1999 | Shiveley et al. |
| 5,873,869 A | 2/1999 | Hammons et al. |
| 5,899,893 A | 5/1999 | Dyer et al. |
| 5,904,675 A | 5/1999 | Laux et al. |
| 5,948,829 A | 9/1999 | Wallajapet et al. |
| 5,985,432 A | 11/1999 | Wang et al. |
| 5,985,434 A | 11/1999 | Qin et al. |
| 6,019,871 A | 2/2000 | Rökman et al. |
| 6,027,795 A | 2/2000 | Kabra et al. |
| 6,033,769 A | 3/2000 | Brueggemann et al. |
| 6,071,580 A | 6/2000 | Bland et al. |
| 6,083,211 A | 7/2000 | DesMarais |
| 6,103,358 A | 8/2000 | Brüggemann et al. |
| 6,261,679 B1 | 7/2001 | Chen et al. |

\* cited by examiner

500um 3kv 10x kc4.tif
KC Foam 35% SAM

ABSORBENT MATERIALS HAVING IMPROVED FLUID INTAKE AND LOCK-UP PROPERTIES

CROSS REFERENCE TO RELATED APPLICATION

This application is a continuation-in-part of U.S. patent application Ser. No. 10/017,683, filed Dec. 14, 2001.

FIELD OF THE INVENTION

This invention relates to absorbent composites having improved multifunctional absorbent properties useful in absorbent articles. More specifically this invention relates to absorbent composites having rapid fluid intake and rapid lock-up of liquid.

BACKGROUND OF THE INVENTION

Various absorbent materials and structures are known in the art. Important characteristics of commercial absorbent materials and structures include either a high rate of fluid intake or rapid lock-up of liquid, but not both. Nonwoven surge materials, as taught in U.S. Pat. No. 5,490,846 to Ellis et al. and in U.S. Pat. No. 5,364,382 to Latimer, for example, have excellent intake functionality but typically almost no fluid retention properties. Current commercial diaper absorbent cores comprising an absorbent fluff and superabsorbent material combination typically provide good fluid absorbency but, often depending on the core density, typically poor fluid intake.

High liquid intake rate composites can be achieved through a variety of ways. High stiffness superabsorbent particles, high stiffness fibers, and/or stabilization of the composite structure have been shown to be effective at achieving high intake rates and sometimes maintaining that rate over multiple insults. However, swelling kinetics of the superabsorbent particles that dictate the speed of liquid lock-up into the superabsorbent particles are typically inadequate.

A typical disposable absorbent product generally has a composite structure including a topsheet, a backsheet, and an absorbent structure between the topsheet and backsheet. In current commercial absorbent structures layers of different materials, such as a surge layer and an absorbent core layer, are required to provide desired fluid handling characteristics of high liquid intake and high liquid lock-up. The result may be an absorbent article with many production steps and high cost. There is a need for an absorbent composite having enhanced fluid intake and high liquid lock-up characteristics that could be used alone or in combination with other materials in an absorbent article.

SUMMARY OF THE INVENTION

This invention is directed to absorbent composites having improved fluid handling properties and methods of making the absorbent fibrous or non-fibrous structure. The absorbent fibrous composites of this invention have a high intake rate of liquid and a high liquid lock-up fraction. Absorbent composites of this invention can be any foam, foam-like composite, airlaid composite, airformed composite, wet-formed composite, or combinations thereof. Absorbent composites of this invention can be modified using treatments such as ultraviolet radiation, ultrasonic, microwave radiation, and/or in-situ polymerization treatment to enhance liquid intake and lock-up performance.

In one embodiment of the invention, the absorbent composite includes a freeze-dried absorbent composite. The absorbent composite is made by forming a slurry comprising a water-insoluble fiber, and a binding agent. An absorbent material is then added to the slurry. The solution is cooled to a temperature between about −50° C. and 0° C. at a cooling rate effective to freeze the water. The frozen water is removed through sublimation and a fibrous absorbent composite is recovered. The freeze-dried composites of this invention have an intake rate of at least about 1.9 cubic centimeters (cc) of liquid/second at 80% composite saturation and a liquid lock-up fraction of at least about 0.70 at 50% superabsorbent saturation, as determined by test procedures described below.

In one embodiment of this invention, the absorbent composite includes an airformed absorbent composite. The airformed composite is formed by mixing superabsorbent material and a fibrous material and using an airforming machine to lay down a web of intermingled fibers and superabsorbent materials onto a porous tissue. The airformed absorbent composites of this invention have an intake rate of at least about 1.9 cc liquid/second at 80% absorbent composite saturation and a liquid lock-up fraction of at least about 0.70 at 50% superabsorbent saturation, as determined by test procedures described below.

In another embodiment of this invention, the absorbent composite is formed from a non-fibrous matrix. The non-fibrous absorbent composites of this invention have an intake rate of at least about 1.9 cc liquid/second at 80% absorbent composite saturation and a liquid lock-up fraction of at least about 0.70 at 50% superabsorbent saturation, as determined by test procedures described below.

Binding agents can be used in absorbent composites of this invention to provide strength to the absorbent composite structure both in the dry state and the wet state. Binding agents are water-insoluble in the absorbent composite and can bind the fibers of the absorbent composite together. Binding agents can be water-swellable and can be used to enhance liquid intake and liquid lock-up. A crosslinking agent may be needed to insolubilize a water-soluble binding agent after formation of the absorbent composite.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

Definitions

Figure 1:
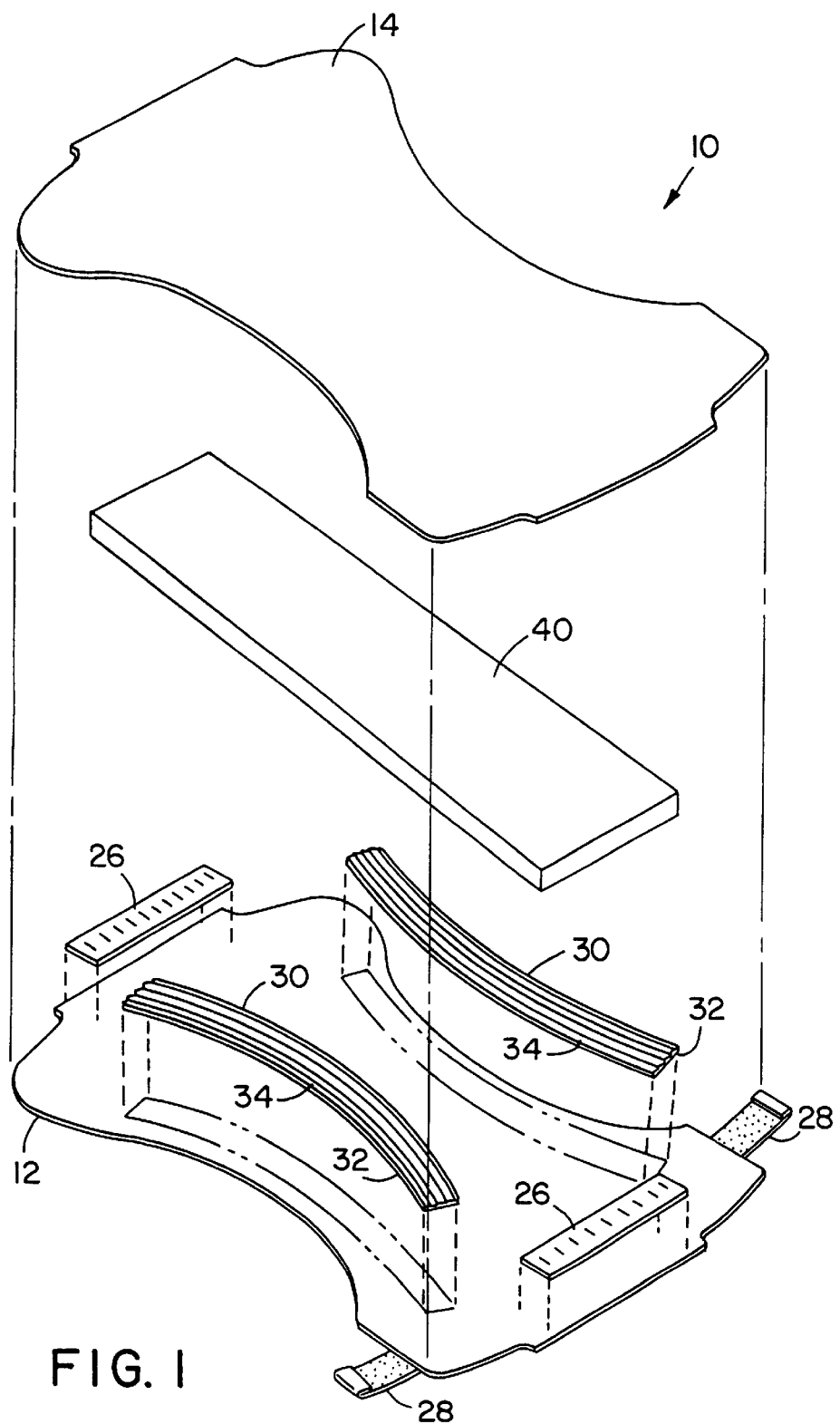
FIG. 1 is an exploded perspective view of a diaper according to one embodiment of this invention.

Within the context of this specification, each term or phrase below will include the following meaning or meanings.

"Foam" refers to two-phase gas-solid systems that have a supporting solid lattice of cell walls that are continuous throughout the structure. The gas, typically air, phase in a foam is usually distributed in void pockets often called cells. "Open-cell foams" are polymeric materials having substantial void space in the form of cells defined by a plurality of mutually connected, three dimensionally branched webs of polymeric material. The cells typically have openings to permit fluid communication from one cell to another. In other words, the individual cells of the foam are not completely isolated from each other by the polymeric material of the cell walls. The cells in such substantially open-celled foam structures have intercellular openings which are large enough to permit fluid transfer from one cell to another within the foam structure. For purposes of this invention, a foam material is "open-celled" if at least 50%, and desirably at least 80%, of the cells in the foam structure that are at least about 1 micron size are in fluid communication with at least one adjacent cell.

"Superabsorbent saturation level" refers to the amount of liquid the superabsorbent material has absorbed as compared to, as a percentage, the total amount of liquid, or the total saturation level, the superabsorbent material is able to absorb. A 50% superabsorbent saturation level thus means that the superabsorbent material has absorbed 50% of the total amount of liquid the superabsorbent material is able to absorb.

"Absorbent composite saturation level" refers to the amount of liquid the absorbent composite (i.e. freeze-dried composite) has absorbed as compared to, as a percentage, the total amount of liquid, or the total saturation level, the absorbent composite is able to absorb. An 80% absorbent composite saturation level thus means that the absorbent composite has absorbed 80% of the total amount of liquid the absorbent composite is able to absorb. "Freeze-dried composite saturation level" is equivalent to "absorbent composite saturation level" and is used when the absorbent composite described is a freeze-dried composite.

"Capillary size" refers to the size of the open cells in the fibrous composites of this invention. The capillaries, or interconnected open cells, are the passage ways through which fluids are taken into the absorbent fibrous composites.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Superabsorbent material" refers to a water-swellable, water-insoluble organic or inorganic material capable, under the most favorable conditions, of absorbing at least about 10 times its weight, preferably at least about 30 times its weight in an aqueous solution containing 0.9% by weight sodium chloride. Superabsorbent material can comprise particles, fibers, and/or other structural forms. "Water-swellable, water-insoluble" refers to the ability of a material to swell to a equilibrium volume in excess water but not dissolve into the water. The water-swellable, water-insoluble material generally retains its original identity or physical structure, even in a highly expanded state during the absorption of water.

"Water soluble" refers to materials which substantially dissolve in excess water to form a solution, thereby losing its initial form and becoming essentially molecularly dispersed throughout the water solution. As a general rule, a water-soluble material will be free from a substantial degree of crosslinking, as crosslinking tends to render a material water insoluble. A material that is "water insoluble" is one that is not water soluble according to this definition.

"Solvent" refers to a substance, particularly in liquid form, that is capable of dissolving a polymer used herein to form a substantially uniformly dispersed mixture at the molecular level.

The term "absorbent article" includes without limitation diapers, training pants, swim wear, absorbent underpants, baby wipes, adult incontinence products, feminine hygiene products, medical garments, underpads, bandages, absorbent drapes, and medical wipes, as well as industrial work wear garments.

The term "non-fibrous" includes, without limitation, absorbent structures containing no fibrous material, such as an open-celled polymeric foam.

These terms may be defined with additional language in the remaining portions of the specification.

This invention relates to absorbent composites having a fibrous or a non-fibrous matrix and superabsorbent material. The absorbent composites of this invention have both a high liquid intake into the composite, and a rapid lock-up of liquid. "Intake rate" refers to the volume of liquid that is transferred into a composite as a function of time, as determined by a testing procedure described below. The liquid simply must enter into the composite and may be present as free liquid in the interstitial space of the absorbent composite, as liquid absorbed into a superabsorbent material, and liquid that has passed through the composite. "Lock-up" refers to the amount of liquid absorbed into the superabsorbent material of the absorbent composite within a predetermined amount of time, as determined by a testing procedure described below. The benefit of a high intake rate, in particular, results in substantial leakage control. The combined benefits of high intake rate and high lock-up percentage result in an absorbent composite which can quickly contain a liquid insult and prevent that liquid from being expelled from the composite under pressure or gravity.

The absorbent composites of this invention may be used alone or in combination with other absorbent layers, such as a surge layer. The absorbent composites are useful in absorbent articles such as diapers, training pants, swim wear, adult incontinence articles, feminine care products, and medical absorbent products.

The absorbent composites of this invention include one or more superabsorbent materials known in the art, and can be formed as a freeze-dried composite, an airformed absorbent composite, a wetformed absorbent composite, or other absorbent fibrous composite. These composites comprise a water-swellable, water-insoluble superabsorbent material and an insoluble fiber. The absorbent composites of this invention can also include one or more superabsorbent materials known in the art, and can be formed as a non-fibrous absorbent composite.

The open porous structure of the absorbent composites of this invention allow for rapid intake. The open porous structure results from the forming process and the nature of the fibers and the superabsorbent stiffness. The superabsorbent materials of this invention may have a high stiffness. "Stiffness" refers to the ability of the superabsorbent material to resist deformation against pressure while in a swollen state. Using a superabsorbent material with a high stiffness provides a more open porous structure because the superabsorbent material does not deform as much during the swelling process as do low stiffness superabsorbents. The fibers of this invention may have a high stiffness. "Stiffness" of the fibers refers to the ability of the fiber to resist bending and deformation while in a wetted state. Using a fiber with a high stiffness provides a more open porous structure because the fiber does not bend and deform as much in the wetted state as do low stiffness fibers. Forming processes of this invention that are used to make absorbent composites also promote a more open porous structure. Forming processes that cause the components of the composite to interact in such a way as to cause the structure to maintain an open porous structure in the wetted state and after the superabsorbent is swollen are useful. Such forming processes include but are not limited to freeze-drying, wet forming, and airforming. The more open structure allows rapid intake of fluid into the composite.

The absorbent composites of this invention exhibit enhanced intake rate and may also exhibit rapid lock-up of liquid. The intake rate of the absorbent composites of this invention is defined at the 80% composite saturation level. The rapid liquid lock-up properties of the absorbent composites of this invention are defined as a fraction of the amount of liquid absorbed by the superabsorbent material over the total added liquid to the absorbent composite at a 50% superabsorbent material saturation level. To determine the intake rate and lock-up fraction of an absorbent composite at these saturation levels it may be necessary to obtain data at various saturation levels and interpolate the intake rate and lock-up fraction at the 80% composite saturation and 50% superabsorbent material saturation levels. These particular saturation levels are important when absorbent composites are used within absorbent articles. Absorbent composites generally have difficulty maintaining intake rate at higher saturation levels, and thus the high saturation levels are where leakage of body fluids from absorbent articles typically occurs. Likewise, the choice of 50% superabsorbent material saturation level as the point to characterize liquid lock-up behavior of this invention is due to the fact that the swelling kinetics of superabsorbent materials typically become relatively slow at these higher swelling levels, thus diminishing the ability to rapidly lock-up liquid. This once again typically results in a tendency for absorbent products to leak.

Absorbent composites according to this invention have an intake rate of at least about 1.9 cubic centimeters liquid/second at 80% composite saturation level and a liquid lock-up fraction of at least about 0.70 at 50% superabsorbent material saturation level. Alternatively, absorbent composites according to this invention have an intake rate of at least about 2.3 cubic centimeters liquid/second at 80% composite saturation level and a liquid lock-up fraction of at least about 0.75 at 50% superabsorbent material saturation level. As another alternative, absorbent composites according to this invention have a intake rate of at least about 2.7 cubic centimeters liquid/second at 80% composite saturation level and a liquid lock-up fraction of at least about 0.80 at 50% superabsorbent material saturation level. As yet another alternative, absorbent composites according to this invention have a intake rate of at least about 3.3 cubic centimeters liquid/second at 80% composite saturation level and a liquid lock-up fraction of at least about 0.80 at 50% superabsorbent material saturation level.

Obtaining the intake rate and lock-up fraction of this invention can be dependent on the specific combination of three characteristics: 1) the structure of the composite (freeze-dried composite, airformed, etc.); 2) the superabsorbent material used; and 3) the fiber type used. As will be seen by the examples below, making a freeze dried composite and an airformed composite from the same superabsorbent material and fiber type results in one composite having intake rate and liquid lock-up of this invention and one that does not.

Absorbent composites of this invention are useful in absorbent articles such as a diaper. FIG. 1 illustrates an exploded perspective view of a typical disposable diaper. Referring to FIG. 1, disposable diaper 10 includes outer cover 12, body-side liner 14, and absorbent core 40 located between body-side liner 14 and outer cover 12. Absorbent core 40 can comprise any of the absorbent composites according to this invention. Outer cover 12 is constructed of conventional non-absorbent materials. By "non-absorbent" it is meant that these materials have an absorptive capacity not exceeding 5 grams of 0.9% by weight aqueous sodium chloride solution per gram of material.

Body-side liner 14 is constructed from highly liquid pervious materials. This layer functions to transfer liquid from the wearer to the absorbent core 40. Suitable liquid pervious materials include porous woven materials, porous nonwoven materials, films with apertures, open-celled foams, and batting. Examples include, without limitation, any flexible porous sheets of polyolefin fibers, such as polypropylene, polyethylene, or polyester fibers; webs of spunbonded polypropylene, polyethylene, or polyester fibers; webs of rayon fibers; bonded carded webs of synthetic or natural fibers; or combinations thereof. The various layers of article 10 have dimensions which vary depending on the size and shape of the wearer.

Attached to outer cover 12 may be waist elastics 26, fastening 28, and leg elastics 30. The leg elastics 30 typically have a carrier sheet 32 and individual elastic strands 34. The diaper of FIG. 1 is a general representation of one basic diaper embodiment. Various modifications can be made to the design and materials of diaper parts. For example, a surge material can be placed between the body-side liner 14 and the absorbent core 40, or placed between the absorbent core 40 and the outer cover 12. Surge material is typically a non-absorbent nonwoven material which has a high intake of fluid and is useful in temporarily storing and distributing fluids to the absorbent material.

Possible construction methods and materials of an embodiment of a diaper such as illustrated in FIG. 1, are set forth in greater detail in commonly assigned U.S. Pat. No. 5,509,915, issued Apr. 23, 1996 in the name of Hanson et al., incorporated herein by reference. Possible modifications to the diaper illustrated in FIG. 1 are set forth in commonly assigned U.S. Pat. No. 5,509,915 and in commonly assigned U.S. Pat. No. 5,364,382, issued Nov. 15, 1994 to Latimer et al.

An absorbent composite according to one embodiment of this invention is a freeze-dried absorbent composite comprising superabsorbent material. The method of making the freeze-dried absorbent composite according to one embodiment of this invention includes forming a slurry of water, a binding material, and a water insoluble fiber material. A water-swellable, water-insoluble superabsorbent material is then added to the slurry and the slurry is cooled to a temperature appropriate to freeze the water. The water is removed from the slurry under a high vacuum while the slurry is still in the frozen state, and a freeze-dried absorbent composite is recovered. Co-pending U.S. Patent Application filed on Dec. 14, 2001, having Ser. No. 10/017,465, discloses embodiments of freeze-dried composites and methods for making freeze-dried composites that can be used to make the freeze-dried composites of this invention, and is herein incorporated by reference.

Suitable freezing temperature for making a freeze-dried fibrous composite is below the freezing point of the slurry solvent used. When water is used as the slurry solvent the temperature should be about 0° C. to about −50° C., suitably from about −5° C. to −50° C., more suitably from about −10° C. to −40° C., and desirably from about −10° C. to −30° C. The selection of temperature is also dependent on the nature and concentration of the slurry. If the temperature selection is too close to the freezing point of the polymer slurry solution the frozen slurry may not have enough strength and may deform under vacuum removal of the solvent. If the temperature drops too far below the solvent freezing point the solvent molecules may form crystals which generally causes substantial cracks in the composite and reduces mechanical properties of the recovered composites.

While freezing the slurry it is important to control the cooling rate of the slurry from room temperature (~23° C.) to freezing temperature. The cooling rate should not exceed a critical cooling rate. "Critical cooling rate" refers to the cooling rate at which, or any rate greater, the slurry, as well as the final absorbent composite, begins to form visible cracks or visible non-uniformity. Critical cooling rate can vary depending upon the freezing point of the solvent used, concentration of slurry, use of a two solvent slurry, crystallizability of the solvent, ratio of insoluble fibers to superabsorbent material, and ratio of fibers to binding agent. A cooling rate slower than the critical cooling rate is preferred and generally results in a much more uniform pore structure and a softer, more flexible absorbent composite, due to the elimination of substantial cracks caused by uneven crystallization of solvent molecules. The cooling rate for an aqueous slurry having a weight ratio of insoluble fibers to soluble polymer greater than 9:1 or a weight ratio of water-swellable superabsorbent material to water-soluble polymer greater than 9:1, should be between about 0.01° C. and 10° C. per minute, suitably between about 0.05° C. to 3° C. per minute, and desirably between about 0.1° C. and 1° C. per minute.

Removal of the frozen solvent is preferably done by vacuum sublimation. Vacuum suitable for this invention is dependent on the volatility of solvent used. Higher vacuum can increase the rate of sublimation and lower vacuum applies a lower pressure on the frozen slurry that can result in less damage and a higher mechanical strength of the resulting composite. Vacuum conditions are desirably less than about 500 millitorrs, or less than about 300 millitorrs, or less than 200 millitorrs, or less than 100 millitorrs. In general, good vacuum can be achieved by either a good quality vacuum pump or a lower condenser temperature, which captures more water vapor. Because sublimation is endothermic, the temperature of the frozen slurry is reduced as water is sublimated under vacuum. This means that the frozen slurry will be even colder and therefore it becomes more difficult to release water molecules. In order to compensate such energy loss, the freeze dryer should be equipped with a heater which provides just enough heat to compensate the energy loss to maintain temperature at a predetermined level.

The freeze-dried composites of this invention suitably have an intake rate of at least about 1.9 cc liquid/second at 80% freeze-dried composite saturation and a liquid lock-up fraction of at least about 0.70 at 50% superabsorbent material saturation. Alternatively, the freeze-dried composites of this invention have an intake rate of at least about 2.3 cc liquid/second at 80% freeze-dried composite saturation and a liquid lock-up fraction of at least about 0.75 at 50% superabsorbent material saturation. As another alternative, the freeze-dried composites of this invention have an intake rate of at least about 2.7 cc liquid/second at 80% freeze-dried composite saturation and a liquid lock-up fraction of at least about 0.80 at 50% superabsorbent material saturation.

As yet another alternative, the freeze-dried composites of this invention have an intake rate of at least about 3.3 cc liquid/second at 80% freeze-dried composite saturation and a liquid lock-up fraction of at least about 0.80 at 50% superabsorbent material saturation.

Figure 3:
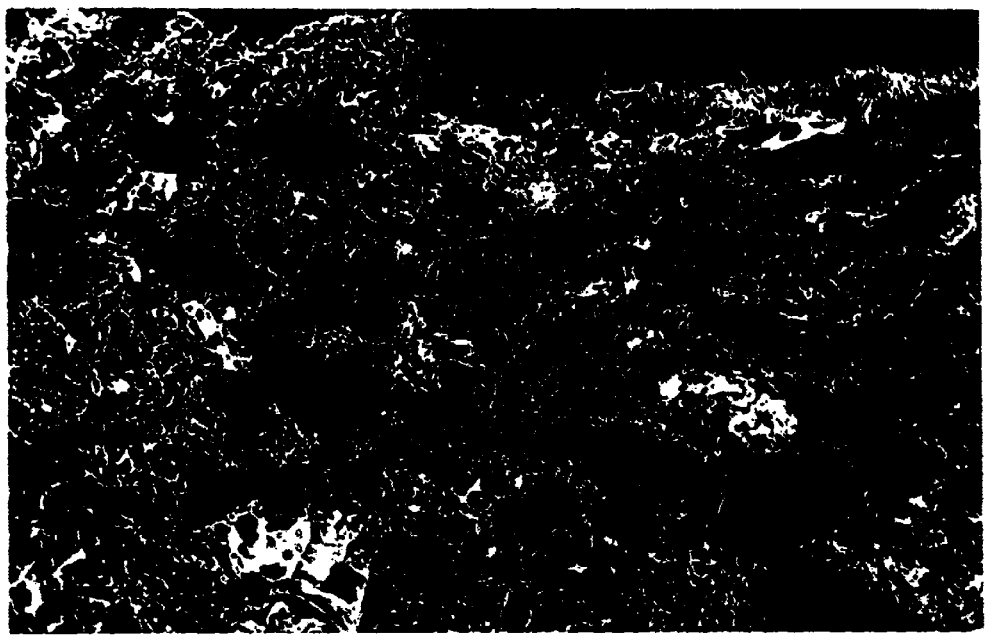
FIG. 3 is a photograph of an absorbent fibrous structure according to one embodiment of the invention.

The resulting composite, as shown in FIG. 3, is a soft freeze-dried absorbent composite including a water-swellable, water-insoluble superabsorbent polymer and a water insoluble fiber. The water-swellable, water-insoluble superabsorbent material is present in the absorbent composite in a weight amount of at least about 10% by weight, suitably from about 10% to 70% by weight, alternatively from about 20% to 60% by weight, or from about 30% to 50% by weight. The water-insoluble fiber is present in the absorbent composite in a weight amount from about 10% to 90% by weight, suitably from about 20% to 80% by weight, or from about 50% to 70% by weight. The binding material is present in the absorbent composite in a weight amount from about 0% to 10% by weight, suitably from about 1% to 8% by weight, and alternatively from about 2% to 5% by weight.

Water-insoluble fibers suitable for the various fibrous absorbent composites of this invention include both natural fibers including without limitation, wood pulp, cotton linter, synthetic fibers including, without limitation, thermoplastic fibers such as polyethylene fibers, polypropylene fibers, poly(ethylene terephthalate), polyester fibers, and elastic fibers such as polyurethane fibers. Hydrophilic fibers are preferred due to their wettability characteristics. Hydrophobic fibers can be used and are preferably treated with surfactants or other effective treatment to alter surface chemistry to increase wettability.

Fiber size directly affects capillary structure of the final absorbent composite. Generally, the larger the fiber size, the larger the capillary size, and when the capillary size gets larger, the ability to move liquid to high heights against gravity is diminished. Oppositely, smaller fiber size generally provides smaller capillary size which can move liquid up to high heights against gravity, but the rate of liquid movement may be negatively impacted. Therefore, an appropriate fiber size choice is critical based on the final function desired. Generally, larger and stiffer fibers are preferred because they lead to structures with larger capillaries that would improve the intake rate of the composite. Fibers useful in this invention have a diameter of about 1 microns to 100 microns, suitably about 1 microns to 50 microns, and desirably about 10 microns to 30 microns.

Water-swellable, water-insoluble superabsorbent materials suitable for all composite structures of this invention include crosslinked anionic and cationic polymers. Anionic polymer examples include without limitation, sodium-polyacrylate, carboxymethyl cellulose (CMC), carboxymethyl polysaccharides including starch, chitin, and other gums, polyaspartic acid salt, maleic anhydride-isobutylene copolymer, and copolymers and admixtures of these polymers. Cationic examples include without limitation, chitosan salts, polyquarternary ammonium salts, polyvinyl amines, and copolymers and admixtures of these polymers. Physical form of the superabsorbent materials can be particulate, fibrous, nonwoven aggregate, printed, coated, or other forms.

Figure 2:
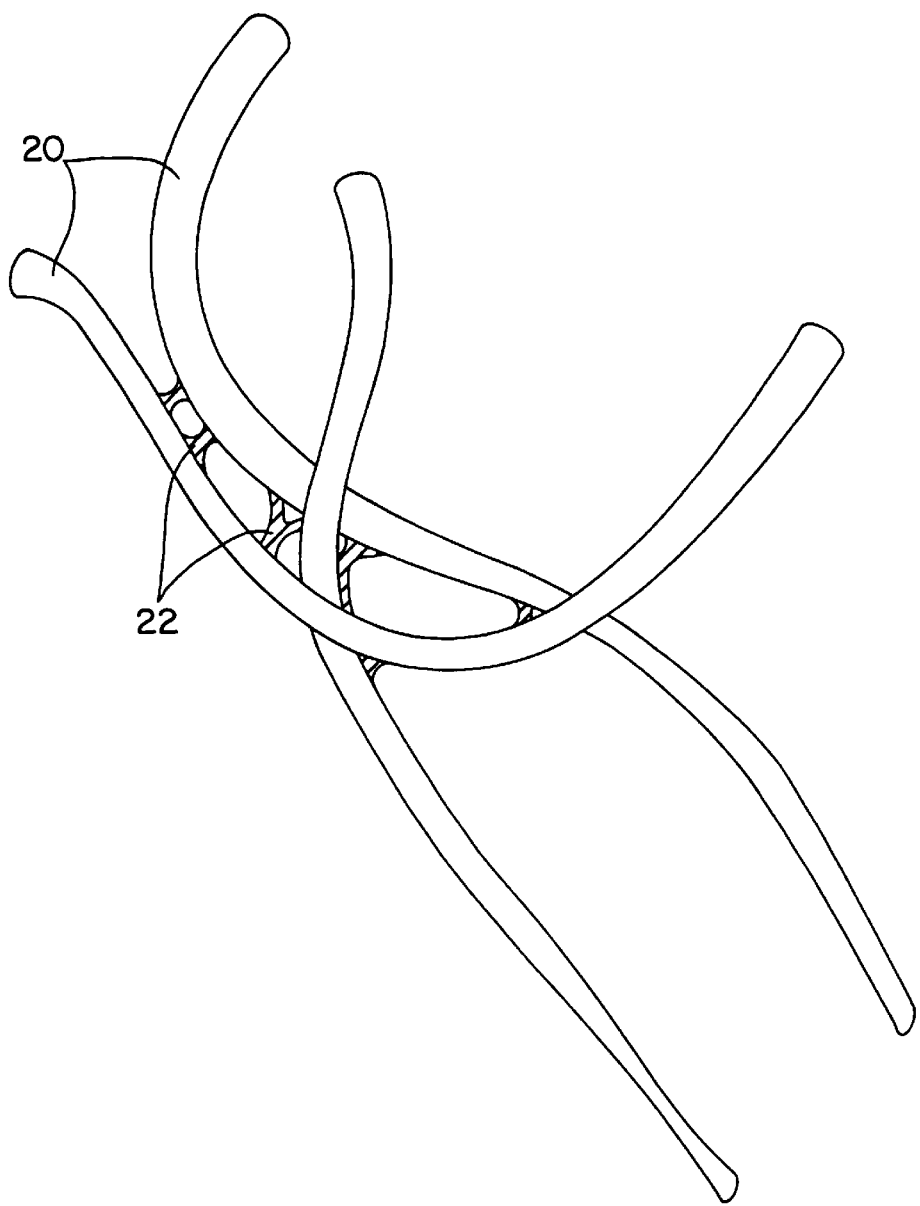
FIG. 2 shows absorbent fibers in an absorbent structure according to one embodiment of this invention.

Binding materials provide strength to the absorbent fibrous composite both in the dry state and the wet state. Binding materials are typically water-soluble or dispersible in the slurry and water-insoluble in the absorbent fibrous composite after freeze-drying and/or heat curing. Binding materials bind the water-insoluble fibers and the superabsorbent materials together. As shown in FIG. 2, fibers 20 are held together in the fibrous absorbent composite structure by binding material polymers 22. The binding material may be water-swellable or not water-swellable. For use in absorbent articles the binding material is preferably water-swellable. Preferred binding material polymers are hydrophilic and substantially water-insoluble in the absorbent fibrous composite, providing desired wet strength of the fibrous composite.

For swellable binding materials, high molecular weight ionic polymers such as sodium-polyacrylate, carboxymethyl cellulose, and chitosan salt are useful in that they provide strength and absorbency to the freeze-dried composite. Other swellable binding materials include isobutylene-maleic anhydride copolymers, polyvinyl amines, polyquarternary ammoniums, polyvinyl alcohols, hydroxypropyl celluloses, polyethylene oxides, polypropylene oxides, polyethylene glycols, modified polysaccharides, proteins, and combinations thereof. Non-swellable, low molecular weight binding materials include poly(aminoamide) epichlorohydrin polymer, such as KYMENE® (available from Hercules Inc., Chicopee, Mass.), latex, and other adhesives. Other non-swellable binding materials include any wet strength resins used in the paper making industries and any type of adhesive material. If an adhesive is used it is preferred that the adhesive is hydrophilic.

A crosslinking agent may be needed to insolubilize a water-soluble binding material after formation of the absorbent composite structure. Crosslinking agents are typically water-soluble. Suitable crosslinking agents include organic compounds comprising at least two functional groups capable of reacting with at least one of carboxyl, carboxylic acid, amino, and/or hydroxyl groups. Examples of this type of crosslinking agents include without limitation, diamines, polyamines, diols, polyols, polycarboxylic acids, and polyoxides. Another suitable crosslinking agent is a metal ion with more than two positive charges, including without limitation, $Al^{3+}$, $Fe^{3+}$, $Ce^{3+}$, $Ce^{4+}$, $Ti^{4+}$, $Zr^{4+}$, and $Cr^{3+}$. When cationic polymer binding agents are used, polyanionic substances are suitable crosslinking agents. Polyanionic substances include without limitation, sodium-polyacrylate, carboxymethyl cellulose, and polymers including the phosphate anion —$PO_4^{3-}$.

In one embodiment of this invention, the method of making a freeze-dried absorbent composite includes forming a slurry of water and a water insoluble fiber material with no binding material. A water-swellable, water-soluble superabsorbent precursor is then added to the slurry and the slurry is cooled to a temperature appropriate to freeze the water. The water is removed from the slurry under high vacuum sublimation, and an absorbent composite is recovered.

When the water-soluble superabsorbent precursor is used, there is no need to add a binding material. The superabsorbent material will act as the binding material when the water-soluble superabsorbent precursor is crosslinked to form a water-swellable, water-insoluble network after composite production. The resulting composite is also a soft absorbent composite comprising a water-swellable, water-insoluble superabsorbent polymer and a water insoluble fiber.

Examples of water-soluble superabsorbent precursors include, without limitation, polyacrylic acid, carboxymethyl cellulose, and chitosan salt. Examples of other superabsorbent precursors include isobutylene-maleic anhydride copolymers, polyvinyl amines, polyquarternary ammoniums, polyvinyl alcohols, hydroxypropyl celluloses, polyethylene oxides, polypropylene oxides, polyethylene glycols, modified polysaccharides, proteins, and combinations thereof.

When a superabsorbent precursor or a water-soluble binding agent is used in this invention, a crosslinking agent is added. After the recovery of the freeze-dried fibrous composite the composite may require treatment to induce the crosslinking to provide a water-insoluble superabsorbent material or a water-insoluble binding agent. Suitable post composite treatment includes without limitation, heat curing at temperature greater than 60° C., ultraviolet radiation, microwave radiation, steam or high pressure, electronic beam radiation, organic solvents, and humidity treatment.

Absorbent composites of another embodiment of this invention are airformed absorbent composites. Airformed absorbent composites are made by combining superabsorbent particles and matrix fibers into an airforming former unit to mix and lay down a web of intermingled superabsorbent particles and matrix fibers. The web of intermingled superabsorbent particles and matrix fibers is formed directly onto a porous sheet of tissue. One example of a suitable porous tissue is designated as 9.8 pound White Forming Tissue available from American Tissue, Inc., Neenah, Wis. The airformed absorbent composite can then be compressed to a desired density by a Carver Press. A suitable airformed absorbent composite density is between about 0.05 gram/cubic centimeter (g/cc) and 0.5 g/cc, a more suitable density is between about 0.1 g/cc and 0.4 g/cc, and a preferred density is between about 0.15 g/cc and 0.3 g/cc. The water-swellable, water-insoluble superabsorbent material is present in the absorbent composite in a weight amount of at least about 10% by weight, suitably from about 10% to 70% by weight, desirably from about 20% to 60% by weight, and preferably from about 30% to 50% by weight. The water-insoluble fiber is present in the absorbent composite in a weight amount from about 10% to 90% by weight, suitably from about 20% to 80% by weight, and desirably about 50% to 70% by weight.

Absorbent composites of another embodiment of this invention are wetformed absorbent composites. Wetformed absorbent composites are formed by processes well known in the art. One example of a process for making wetformed absorbent composite is disclosed in U.S. Pat. No. 5,651,862, issued to Anderson et al. on Jul. 29, 1997, herein incorporated by reference. Wetformed composites are generally formed by mixing fibers, absorbent materials, and other possible additives such as binder materials into a liquid medium. The medium plus the fibers, absorbent materials, and the other possible additives are conveyed onto a web forming porous substrate, and the medium is removed by vacuum. The water-swellable, water-insoluble superabsorbent material is present in the absorbent composite in a weight amount of at least about 10% by weight, suitably about 10% to 70% by weight, desirably about 20% to 60% by weight, and preferably about 30% to 50% by weight. The water-insoluble fiber is present in the absorbent composite in a weight amount from about 10% to 90% by weight, suitably about 20% to 80% by weight, and desirably about 50% to 70% by weight.

In the various embodiments of this invention, many suitable types of wettable, hydrophilic fibrous materials can be used to form the absorbent composites. Suitable matrix fibers include without limitation, naturally occurring organic fibers composed of inherently wettable material, such as cellulose fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. Combinations of various fibers can also be used in absorbent composites of this invention.

Other embodiments of this invention may include a non-fibrous matrix. One example of a non-fibrous matrix is an open-celled foam. Absorbent composites including a non-fibrous matrix can be formed by mixing superabsorbent and the non-fibrous matrix in such a way as to distribute the superabsorbent uniformly or non-uniformly throughout the non-fibrous matrix. The water-swellable, water-insoluble superabsorbent material may be present in the absorbent composite in a weight amount of at least about 10% by weight, suitably about 10% to 70% by weight, desirably about 20% to 60% by weight, and preferably about 30% to 50% by weight. The non-fibrous matrix may be present in the absorbent composite in a weight amount about 10% to 90% by weight, suitably about 20% to 80% by weight, and desirably about 50% to 70% by weight.

Suitable superabsorbent materials include, without limitation, the alkali metal and ammonium salts of poly (acrylic acid) and poly(methacrylic acid), poly (acrylamides), poly(vinyl ethers), (maleic anhydride copolymers with vinyl ethers and alpha-olefins, polyvinyl pyrrolidone), poly(vinylmorpholinone), poly(vinyl alcohol), and mixtures and copolymers thereof. Current commercial superabsorbent materials can be modified to improve the absorption characteristics for use in the absorbent composites of this invention. One method of modifying superabsorbent materials is by using freeze-drying techniques as disclosed in co-pending U.S. Patent Application filed by Express Mail No. EV068478187 on Nov. 8, 2002, and having Ser. No. 10/291,237, herein incorporated by reference, and similar to those described above. Freeze-dried superabsorbent materials can be used with airforming techniques, wetlaying techniques, and other composite forming methods to obtain absorbent composites having the improved absorbent properties of this invention. One example of such a modified commercial superabsorbent material is a modified freeze-dried superabsorbent material FAVOR® SXM 9543, available in unmodified form from Stockhausen, Inc., Greensboro, N.C. Freeze-dried superabsorbent materials can be obtained by absorbing an amount of water or other solvent, freezing the swollen superabsorbent material, and removing the water by sublimation using a freeze-drier or similar device. One method for freeze-drying the FAVOR® SXM 9543 is described below.

Further polymers suitable for use in absorbent composites include, without limitation, natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic polymers can also be useful in this invention.

Other superabsorbent compositions generally suitable only for dry processes include (1) an acidic water-swellable, water-insoluble polymer and a basic neutralization agent; (2) a basic water-swellable, water-insoluble polymer and an acidic neutralization agent; or (3) an acidic water-swellable, water-insoluble polymer and a basic water-swellable, water-insoluble polymer. These mixtures of superabsorbent compositions are capable of neutralizing each other between the acidic and basic components in-situ upon urine saturation in the absorbent products. Such in-situ neutralization process enhances absorbency of the composition, exhibits a capability of removing salt from the urine or other body fluid, reduces overall cost of the absorbent composition due to the use of low-cost non-polymer based neutralizing agents. Suitable acidic water-swellable, water-insoluble polymers include functional groups that are capable of being converted to anions. Such functional groups include, but are not limited to, carboxylic acid, sulfonic acid, phosphoric acid. Suitably, the functional groups are carboxylic acid groups. Examples of suitable acidic polymer include polyacrylic acid, carboxymethyl cellulose, isobutylene-maleic anhydride copolymer, polyaspartic acid, polyglutamic acid, polyacrylamido methylpropane sulfonic acid, polyvinyl acetic acid, polyvinyl phosphonic acid, polyvinyl sulfonic acid, carrageenan, and alginic acid. Suitable basic water-swellable, water-insoluble polymers include functional groups that are capable of being converted to cations. Such functional groups include, but are not limited to, primary, secondary, or tertiary amino groups, quaternary ammonium groups, imino groups, imido groups. Suitably, the basic functional groups are quaternary ammonium groups and primary amino groups. Examples of suitable basic polymers include polyvinyl amines, polyallylamines, polydiallyldimethyl ammonium hydroxide, chitosan, polyethylene imines, polyasparagins, polyglutamines, polylysines, and polyarginines. Suitable acidic neutralizing agents include both acidic water-swellable, water-insoluble polymers listed above and non-polymer based acidic compounds. These non-polymer based acidic compounds include organic acidic material such as aliphatic and aromatic acids, for example, citric acid, glutamic acid or aspartic acid, and inorganic acids such as metallic oxides, for example, aluminum oxide, and salts such as iron chloride, calcium chloride, and combinations of any of these. Suitable basic neutralizing agents include both basic water-swellable, water-insoluble polymers listed above and non-polymer based basic compounds. These non-polymer based basic compounds include organic basic material such as organic salts, for example, sodium-citrate, and aliphatic and aromatic amines, imines, and amides, and inorganic bases such as metallic oxides, for example, sodium oxides, hydroxides, for example, sodium hydroxide, salts such as sodium carbonate and sodium bicarbonate, and combinations of any of these. Because two components can neutralize each other, it is important that these absorbent compositions avoid any contact with aqueous liquid in the processes of superabsorbent material preparation and absorbent product manufacturing. Contact of water triggers neutralization and therefore eliminates the benefits of the absorbent compositions.

The airformed, wetformed, and non-fibrous absorbent composites of this invention have an intake rate of at least about 1.9 cc liquid/second at 80% absorbent composite saturation and a liquid lock-up fraction of at least about 0.70 at 50% superabsorbent material saturation. Alternatively, the airformed, wetformed, and non-fibrous absorbent composites of this invention have an intake rate of at least about 2.3 cc liquid/second at 80% absorbent composite saturation and a liquid lock-up fraction of at least about 0.75 at 50% superabsorbent material saturation. As another alternative, the airformed, wetformed, and non-fibrous absorbent composites of this invention have an intake rate of at least about 2.7 cc liquid/second at 80% absorbent composite saturation and a liquid lock-up fraction of at least about 0.80 at 50% superabsorbent material saturation. As yet another alternative, the airformed, wetformed, and non-fibrous absorbent composites of this invention have an intake rate of at least about 3.3 cc liquid/second at 80% absorbent composite saturation and a liquid lock-up fraction of at least about 0.80 at 50% superabsorbent material saturation.

EXAMPLES

To demonstrate this invention, five freeze-dried composite samples and five airformed composite samples were made. Table 1 summarizes the compositions of each freeze-dried composite sample made by the following process. For each sample an amount of distilled water listed in Table 1 was poured into a 4 liter HOBART® mixer, Model N50, manufactured by Hobart Canada of North York, Ontario, Canada. The mixer has 3 mixing settings. The mixer was initially set at a relatively slow mixing rate (setting 1) and, while stirring, an amount of wood pulp fluff, available from Bowater Corporation of Coosa Pines, Ala., and designated CR-1654, listed in Table 1 was added to the appropriate water amount. Then the appropriate amount of binder material from Table 1, carboxymethyl cellulose, available from Aqualon Company of Wilmington, Del., designated CMC-7H, was slowly added into the mixer. The addition of the binder material was slow enough to prevent agglomeration of the carboxymethyl cellulose powder.

After mixing for about two minutes, the mixer speed was increased to mixer setting 2. After mixing for an additional five minutes at mixer setting 2 the superabsorbent material, DRYTECH® 2035, available from Dow Chemical Company of Midland, Mich., was added into the mixer and mixed for about 10 seconds at mixer setting 2. The resulting uniform slurries for each sample were each poured into a separate 25.6 cm wide, 51.2 cm long, and 5.2 cm deep stainless steel pan. Each pan was put into a VirTis Genesis Freeze Dryer, Model 25 EL, manufactured by VirTis of Gardiner, N.Y. The samples were freeze dried in the freeze dryer at a shelf temperature of below −50° C., a condenser temperature of below −70° C., and a vacuum of less than 100 millitorrs. The samples were freeze dried between 2 to 3 days depending upon the total loading of frozen water in the dryer. The freeze dried composite samples were then heat treated at 130° C. for two hours to insolubilize the binder material.

TABLE 1

| Sample No. | Superabsorbent Material (g) | Wood Pulp Fluff (g) | Binder Material (g) | Water (g) |
| --- | --- | --- | --- | --- |
| 1 | 28.3 | 28.3 | 6.3 | 1500 |
| 2 | 28.3 | 28.3 | 6.3 | 2000 |
| 3 | 28.3 | 28.3 | 6.3 | 2500 |
| 4 | 16.8 | 39.8 | 6.3 | 1500 |
| 5 | 39.8 | 16.8 | 6.3 | 1500 |

An airformed composite, Sample 6, also made from DRYTECH® 2035, and commercially available diaper samples, Samples 7 and 8, were prepared as a comparison to freeze-dried composite Samples 1–5 and the airformed composites, Samples 9 and 10, described below. Sample 6 was prepared by combining 1.20 grams of DRYTECH® 2035 superabsorbent material with 1.20 grams wood pulp fibers, designated as CARESSA® 1300, available from Buckeye Corporation of Memphis, Tenn., in an airforming handsheet former unit. The airforming handsheet former unit mixed the materials and formed a web of intermingled superabsorbent particles and fibers directly onto a porous sheet of tissue. The tissue was a 9.8 pound White Forming Tissue available from American Tissue Inc., Neenah, Wis. A second layer of tissue was placed above the web following web formation. The airformed composite of Sample 6 was 7.68 cm in diameter and was compressed to a density of 0.2 g/cc using a Carver Press.

The commercially available diapers tested were HUGGIES® Supreme Step-3 (Bag Code NM034102b0545-1900), designated Sample 7, and PAMPERS® Premium Size-2 (Bag Code 1121U017261559), designated Sample 8. To obtain samples for testing, the diaper was placed on a die cutting device and a 7.68 cm diameter sample was taken from the target area of the diaper. The centerpoint of the 7.68 cm die cut sample was 16.64 cm from the front end of the absorbent pad and spaced in the middle of the absorbent pad in the cross-direction. Following punching of the sample, all layers were removed leaving only the superabsorbent-fluff layer of the products.

Samples 9 and 10, airformed composites according to this invention, and Samples 11 and 12, airformed composites not having the composite properties of this invention included for comparison, were made using modified FAVOR® SXM 9543 superabsorbent material. The FAVOR® SXM 9543 was modified by freeze-drying according to the following method. An amount of distilled water was added into a one gallon HOBART® mixer (Model N50, manufactured by Hobart Canada, Ontario, Canada). 100 grams of FAVOR® SXM 9543 superabsorbent particles were added into the mixer while the stirrer was on. After stirring for about 2 minutes, the swollen superabsorbent particles were discharged into a pan (10 inches by 20 inches; 25.4 centimeters by 50.8 centimeters) to form a uniform thin layer. The pan was placed into a VirTis Genesis freeze dryer (Model 25 EL) available from The VirTis Inc. of Gardiner, N.Y. The superabsorbent material was freeze dried in the freeze dryer at a shelf temperature of less than −50° C., a condenser temperature of less than −70° C., and a vacuum of less than 100 millitorrs.

The modified freeze-dried superabsorbent particles of Samples 9 and 11 were made as described above by absorbing 200 grams of distilled water into 100 grams of FAVOR® SXM 9543 (swelling level of 2 grams/gram) and freeze-drying. The modified freeze-dried superabsorbent particles of Samples 10 and 12 were made as described above by absorbing 500 grams of distilled water into 100 grams of FAVOR® SXM 9543 (swelling level of 5 grams/gram) and freeze-drying.

Sample 9 was prepared by combining 1.20 grams of the appropriate modified freeze dried FAVOR® SXM 9543 superabsorbent material with 1.20 grams wood pulp fibers, designated as CR-1654, available from Bowater Corporation, Coosa Pines, Ala., in an airforming handsheet former unit. The airforming handsheet former unit mixed the materials and formed a web of intermingled superabsorbent particles and fibers directly onto a porous sheet of tissue. The tissue was a 9.8 pound White Forming Tissue available from American Tissue Inc. A second layer of tissue was placed above the web following web formation. The airformed composite of Sample 9 was 7.68 centimeter in diameter and was compressed to a density of 0.2 gram/cubic centimeter using a Carver Press.

Sample 10 was prepared by combining 1.20 grams of the appropriate modified freeze dried FAVOR® SXM 9543 with 1.20 grams wood pulp fibers, designated as CR-1654, available from Bowater Corporation, Coosa Pines, Ala., in an airforming handsheet former unit. The airforming handsheet former unit mixed the materials and formed a web of intermingled superabsorbent particles and fibers directly onto a porous sheet of tissue. The tissue was a 9.8 pound White Forming Tissue available from American Tissue Inc. A second layer of tissue was placed above the web following web formation. The airformed composite of Sample 10 was 7.68 centimeter in diameter and was compressed to a density of 0.2 grams/cubic centimeter using a Carver Press.

Sample 11 was prepared by combining 1.20 grams of the appropriate modified freeze dried FAVOR® SXM 9543 superabsorbent material with 1.20 grams wood pulp fibers, designated as CARESSA® 1300, in an airforming handsheet former unit. The airforming handsheet former unit mixed the materials and formed a web of intermingled superabsorbent particles and fibers directly onto a porous sheet of tissue. The tissue was a 9.8 pound White Forming Tissue available from American Tissue Inc. A second layer of tissue was placed above the web following web formation. The airformed composite of Sample 11 was 7.68 centimeter in diameter and was compressed to a density of 0.2 gram/cubic centimeter using a Carver Press.

Sample 12 was prepared by combining 1.20 grams of the appropriate modified freeze dried FAVOR® SXM 9543 with 1.20 grams wood pulp fibers, designated as CARESSA®

1300, in an airforming handsheet former unit. The airforming handsheet former unit mixed the materials and formed a web of intermingled superabsorbent particles and fibers directly onto a porous sheet of tissue. The tissue was a 9.8 pound White Forming Tissue available from American Tissue Inc. A second layer of tissue was placed above the web following web formation. The airformed composite of Sample 12 was 7.68 centimeter in diameter and was compressed to a density of 0.2 grams/cubic centimeter using a Carver Press.

Figure 4B:
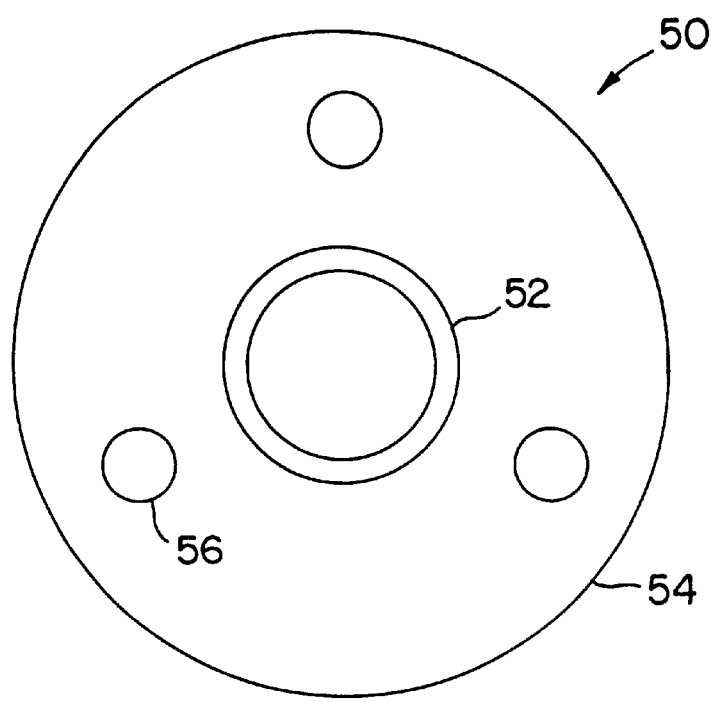
FIG. 4B is a top view of the intake rate testing device.
Figure 4A:
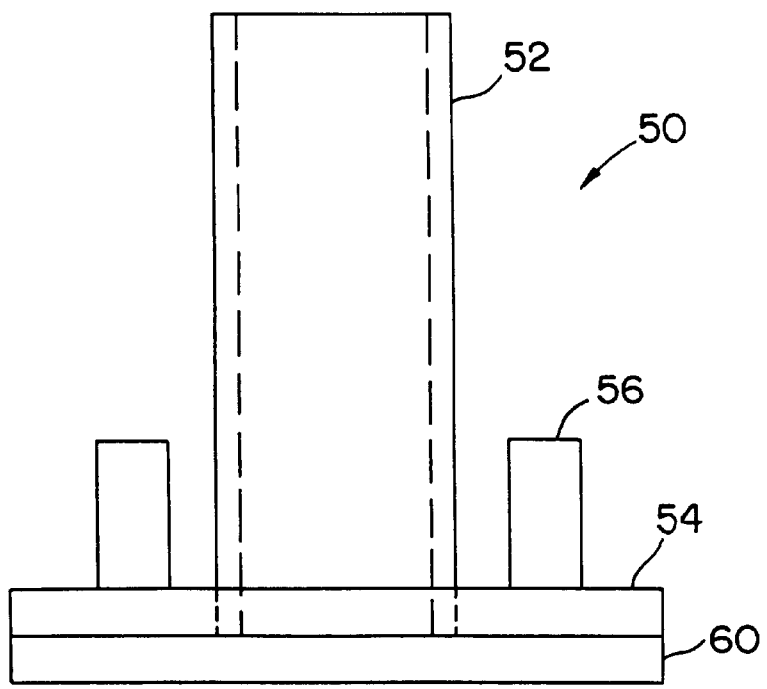
FIG. 4A is a plan view of an intake rate testing device.

Intake rate is determined by pre-weighing a 7.68 cm diameter sample of each of Samples 1–12, and placing the 7.68 cm diameter sample under a cylindrical port device as shown in FIGS. 4A and 4B. FIG. 4A shows cylindrical port device 50 having cylinder 52 and base 54. Cylindrical port device 50 can be made from various materials, such as plastic, and has a weight that will result in pressure being placed on sample 60 below the cylindrical port device 50. As shown in FIG. 4B, additional weights 56 can be placed on base 54 for testing sample 60 at higher pressures. Sample 60 has a diameter substantially equal to the diameter of base 54, which is 7.68 cm for each in the present testing, and is placed under base 54 during testing. The cylindrical port device used in testing Samples 1–12 was made of plastic having a weight of about 39 grams. Additional weights 56, totaling 250 grams, were added to obtain a testing pressure on the samples of about 0.09 pounds per square inch (psi).

Cylinder 52 is hollow with an inner diameter of 2.54 cm, allowing for liquid to be poured into cylinder 52 and contact sample 60 below. For Samples 1–10, 15 cubic centimeters (cc) of 0.9% by weight sodium chloride solution is poured into the cylindrical port device. The time required for the volume of liquid to be absorbed into the samples at the base of the device is recorded. Divide the total charge of 15 cc by the intake time for each sample to obtain the intake rate for that sample.

Figure 5:
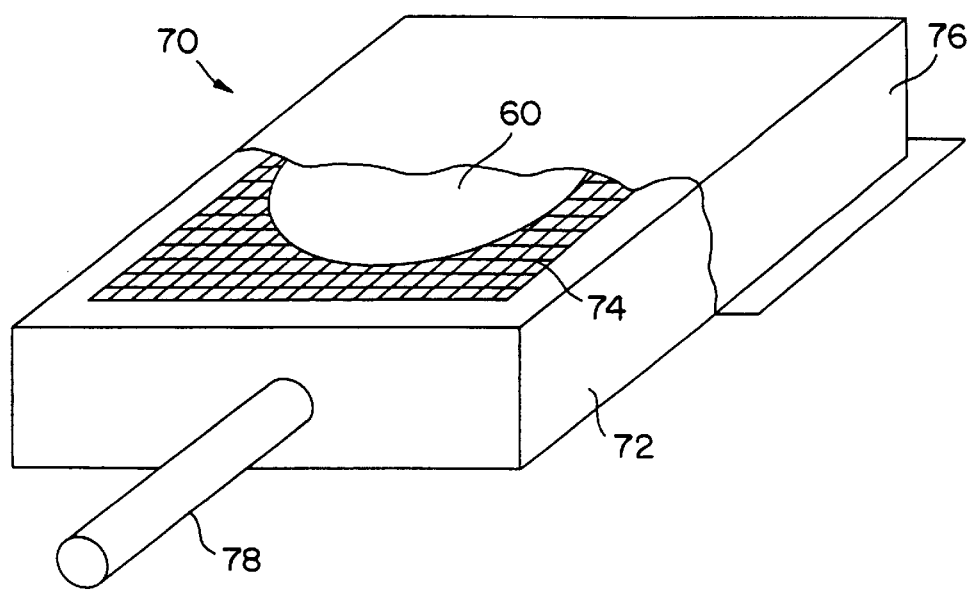
FIG. 5 is a perspective view of a liquid lock-up testing apparatus.

A typical vacuum apparatus useful for lock-up testing is shown in FIG. 5. Vacuum apparatus 70 has base 72 with mesh screen 74 and vacuum tube 78 attached to a vacuum source. Sample 60 is placed onto mesh screen 74, typically a size 100 mesh screen, and sample 60 and base 72 are covered by gas impervious rubber dam 76. A vacuum is applied through vacuum tube 78 and, because rubber dam creates a seal around base 72, the vacuum pulls an amount of liquid from sample 60. The amount of fluid maintained by sample 60 is determined by subtracting the dry weight of the sample from the wet weight of the sample after application of the vacuum, and converting the net weight to milliliters using the density of the test liquid.

For Samples 1–12, lock-up testing is done following the intake rate test by waiting 60 seconds, putting each sample absorbent composite on a vacuum apparatus and applying a vacuum of about minus 13.5 pounds per square inch gauge for two minutes. After applying vacuum for 60 seconds, the mass of sodium chloride solution left in the sample was determined. Determine liquid lock-up by dividing the mass of liquid remaining in the sample by the total initial insult.

The intake and lock-up tests are repeated for each sample three times for a total insult of 45 cubic centimeter (cc) 0.9% by weight sodium chloride solution applied to the sample. After the lock-up testing of each sample, however, the sample composite has been drained of some of the liquid from the intake rate testing insult. Therefore, for the second intake and lock-up tests, a new (although nominally same in composition) sample is used. The second, nominally identical sample is given a first 15 cubic centimeter insult of 0.9% by weight sodium chloride solution insult (equivalent to the amount from the first intake rate test) and, after waiting 15 minutes, a second 15 cubic centimeter insult of 0.9% by weight sodium chloride solution, for a total of 30 cubic centimeter of 0.9% by weight sodium chloride solution. After the second intake rate test a second lock-up test is performed, so the third intake rate test also uses a new, nominally identical sample. The third, nominally identical sample is given a first 15 cubic centimeter insult of 0.9% by weight sodium chloride solution (equivalent to the amount from the first intake rate test), a second of 15 cubic centimeter insult of 0.9% by weight sodium chloride solution after 15 minutes, and, after waiting an additional 15 minutes, a third 15 cubic centimeter insult of 0.9% by weight sodium chloride solution is added to the sample for a total of 45 cubic centimeter of 0.9% by weight sodium chloride solution.

The calculations for intake rate are the same each time. To calculate lockup on subsequent insults, divide the cumulative mass of liquid remaining in the sample after vacuum by the cumulative amount of liquid that has been added to the sample. When the intake rate and lock-up tests are complete a saturation test was conducted on a nominally identical sample to determine total saturation capacity of the absorbent composite.

The liquid saturated retention capacity is determined as follows. The material to be tested is weighed and submerged in an excess quantity of 0.9% by weight sodium chloride solution at standard TAPPI conditions. The material to be tested is allowed to remain submerged for about 20 minutes. After the 20 minute submerging, the material is removed and, referring to FIG. 5, placed on a vacuum apparatus with 0.25 inch diameter openings and covered with size 100 mesh screen 74 which, in turn, is connected to vacuum source 78 and covered with a flexible rubber dam material 76. A vacuum of about −13.5 pounds per square inch gauge is drawn on the vacuum apparatus for a period of about 3 minutes with the use of, for example, house vacuum supply. The material being tested is then removed from the apparatus and weighed. The amount of liquid retained by the material being tested is determined by subtracting the dry weight of the material from the wet weight of the material (after application of the vacuum), converting the weight to milliliters by using the density of the test liquid, and is reported as the liquid saturated retention capacity in milliliters of liquid retained. For relative comparisons, the weight of liquid held (wet weight after application of vacuum minus dry weight) can be divided by the weight of the material 60 to give specific liquid saturated retention capacity in grams of liquid retained per gram of tested material.

The saturation capacity of a superabsorbent material or insoluble fiber is determined by a centrifuge retention capacity test. As used herein, the Centrifugal Retention Capacity (CRC) is a measure of the absorbent capacity of the superabsorbent material or fiber after being subjected to centrifugation under controlled conditions. The superabsorbent sample to be tested is taken from superabsorbent material which is prescreened through U.S. standard #30 mesh and retained on U.S. standard #50 mesh to obtain a particle size of between 300 and 600 microns. Testing a fiber sample is performed "as-is" without fractionation. The CRC can be measured by placing 0.200 grams of the sample material to be tested (moisture content of less than 5 weight percent) into a water-permeable bag which will contain the sample while allowing the test solution (0.9 percent by weight sodium chloride solution) to be freely absorbed by the sample. A heat-sealable tea bag material (grade 542, commercially available from Kimberly-Clark Corporation, Neenah, Wis.) works well for most applications. The bag is formed by folding a 12.7 centimeter by 7.62 centimeter sample of the bag material in half and heat sealing two of the open edges to form a 6.35 by 7.62 centimeter rectangular pouch. The heat seals should be about 0.635 centimeters inside the edge of the material. After the sample is placed in the pouch, the remaining open edge of the pouch is also heat-sealed. Empty bags are also made to be tested with the sample bags as controls. Three sample bags are tested for each superabsorbent material. The sealed bags are placed between two Teflon coated fiberglass screens having 0.635 centimeter openings (Taconic Plastics, Inc., Petersburg, N.Y.) and submerged in a pan of 0.9 percent by weight sodium chloride solution at about 23° C., making sure that the screens are held down until the bags are completely wetted. After wetting, the samples remain in the solution for 30 minutes, at which time they are removed from the solution and temporarily laid on a nonabsorbent flat surface. The wet bags are then placed into the basket of a suitable centrifuge capable of subjecting the samples to a gravitational-force of 300. A suitable centrifuge is a Heraeus Instruments Labofuge 400, having a water collection basket, digital rotations per minute (rpm) gauge, and machined drainage basket adapted to hold and drain the samples. The samples must be placed in opposing positions within the centrifuge to balance the basket when spinning. The bags are centrifuged at a target of 1600 rotations per minute, but within the range of 1500–1900 rotations per minute, for 3 minutes (target gravitational-force of 300). The bags are removed and weighed, with the empty bags (controls) being weighed first, followed by the bags containing the superabsorbent material or fiber. All fluid not locked-up (absorbed) in the superabsorbent material (or the teabag) is centrifuged out of the sample.

The amount of fluid absorbed and retained by the superabsorbent material (or fiber), taking into account the fluid retained by the bag material alone, is the Centrifugal Retention Capacity of the superabsorbent material or fiber, expressed as grams of fluid per gram of material. This calculation is done by the following equation:

$$CRC = \frac{(W_s - W_e - W_d)}{W_d}$$

Where "CRC" is the Centrifugal Retention Capacity of the sample (grams/gram), "$W_s$" is the after centrifuged mass of the teabag and the sample (grams), "$W_e$" is the average after centrifuged mass of the empty teabag (grams), and "$W_d$" is the dry mass of the sample (grams). The CRC measurements for each of three replicate are averaged to provide the CRC value of the material. The centrifuge retention capacity (in gram of fluid per gram of superabsorbent material) of superabsorbent materials used in Samples 1–12 are summarized in Table 2.

TABLE 2

| Sample(s) | Superabsorbent Material (SAM) | Centrifuge Retention Capacity (g/g) |
|---|---|---|
| 1–6 | DRYTECH ® 2035 | 30 |
| 7 | SAM of HUGGIES ® | 30 |
| 8 | SAM of PAMPERS ® | 26 |
| 9 | Freeze-dried FAVOR ® SXM 9543 (2 g/g) | 20.3 |
| 10 | Freeze-dried FAVOR ® SXM 9543 (5 g/g) | 20.2 |
| 11 | Freeze-dried FAVOR ® SXM 9543 (2 g/g) | 20.3 |
| 12 | Freeze-dried FAVOR ® SXM 9543 (5 g/g) | 20.2 |

To separate the superabsorbent material from the fluff of a diaper for CRC testing, the absorbent core of the diaper is first placed in an airlaid handsheet former. The handsheet former takes the relatively dense absorbent core of the product and forms a bulky handsheet on a sheet of tissue. This step in the procedure opens the superabsorbent material/fluff matrix before being placed in a "diaper destroyer" for separation.

The handsheet former has an upper cylinder shaped compartment which is separated from a rectangular lower compartment by a diffusion screen which helps ensure uniform handsheet formation. The absorbent core is separated from the product over the upper compartment of the airlaid handsheet former so that any superabsorbent material or fluff that falls out during removal of the absorbent core goes into the upper compartment. The outer cover, body-side liner, and any surge materials and/or barrier tissues are scraped with a spatula to remove any remaining superabsorbent material or fluff.

The lid is placed on the upper compartment of the handsheet former, and pulsating air in the upper compartment and a vacuum at the bottom of the lower compartment are turned on. The components of the absorbent core are formed into a bulky superabsorbent material/fluff airlaid handsheet on a sheet of tissue located at the bottom of the lower compartment. The tissue provides a barrier to the superabsorbent material and fluff. The handsheet former is operated until no superabsorbent material and approximately 0.5 grams or less of fluff is visible in the upper compartment.

The bulky superabsorbent/fluff pad is then carefully placed in the diaper destroyer. The mechanics of the diaper destroyer are the reverse of the handsheet former. Pulsating air circulating at the bottom of the diaper destroyer breaks apart the bulky pad. The superabsorbent material from the pad collects at the bottom, whereas the fluff is drawn off the top with a vacuum. When most of the fluff has been drawn off, the diaper destroyer is turned off and the superabsorbent material is collected on a nonstick metal tray. Shaking the superabsorbent material on the tray tends to clump the remaining fluff fibers together for easier removal with tweezers, thus avoiding contamination of the superabsorbent material with moisture, etc. from the operator's hands. The collected superabsorbent material is placed in a labeled glass bottle for further characterization.

Because intake rate and liquid lock-up fraction change as a function of saturation, the data should be normalized to a common set of criteria. Using the saturated capacity of the composite, determine the percent saturation of the sample following each insult. For example, a 15 cubic centimeter insult to a sample with a 45 cubic centimeter saturation capacity yields 33% saturation. Plot the intake rate of an absorbent composite as a function of the percent saturation. Interpolate the effective intake rate at the 80% composite saturation level.

Figure 6:
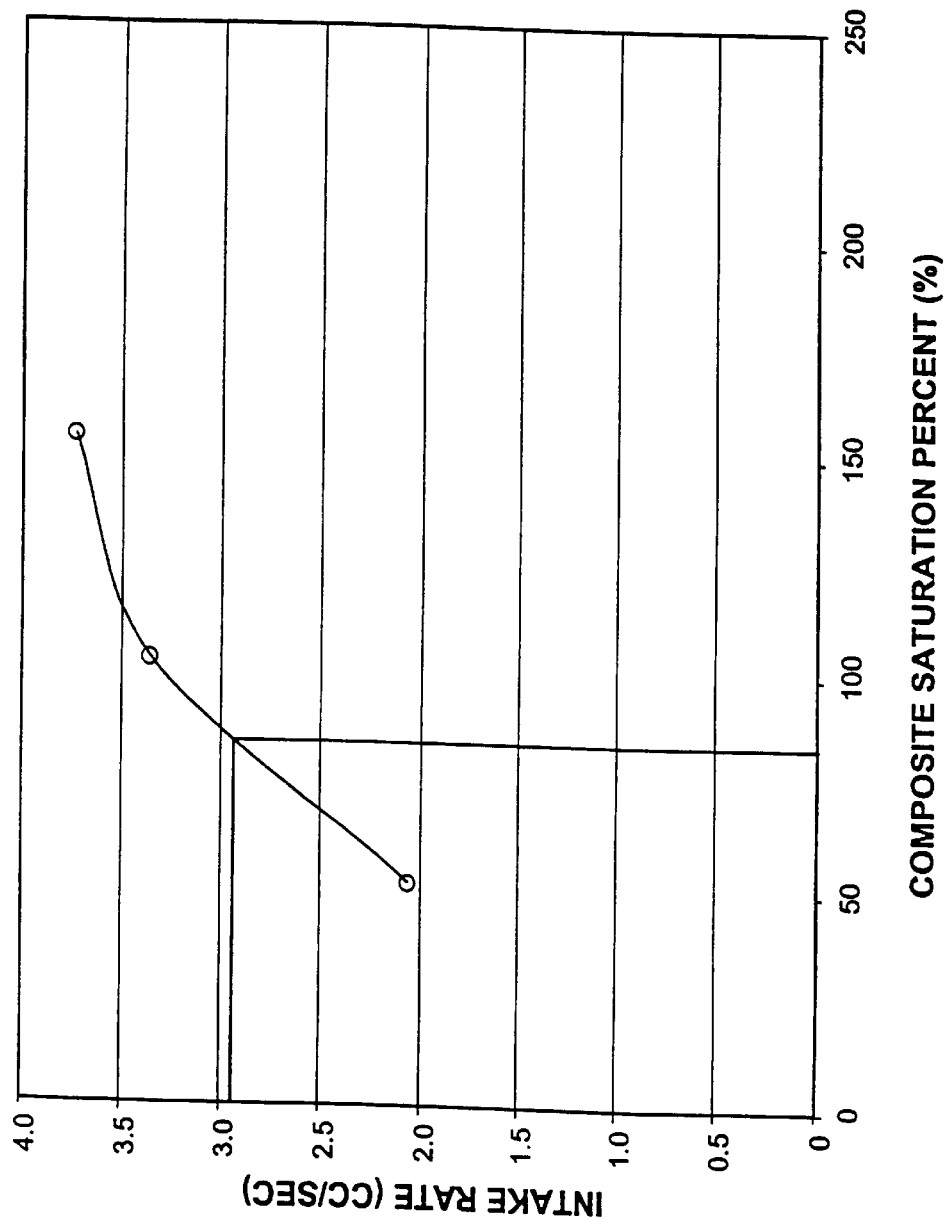
FIG. 6 is a plot of intake rate against composite saturation.

To demonstrate the calculations for determining intake rate at 80% composite saturation, the following is the calculation for determining the intake rate of Sample 6 at 80% composite saturation. The saturation capacity of the 7.68 cm disc of Sample 6 was determined to be 29.13 cubic centimeter liquid. Intake rate is determined by dividing the insult amount (15 cubic centimeter) by the intake time. Table 3 summarizes the intake time and intake rate results for each of the three insults done on Sample 6 during the intake rate test. A composite saturation percent value is calculated for Sample 6 at each of 15 cubic centimeter, 30 cubic centimeter, and 45 cubic centimeter liquid by dividing the cumulative liquid amount (15, 30, or 45 cubic centimeter) by the saturation capacity of the composite and multiplying by 100%. The results are summarized in Table 3. The intake rate data are plotted against the respective composite saturation percent in a scatter plot with smoothed lines. FIG. 6 shows the scatter plot for the values of Table 3 as done using the spreadsheet Microsoft Excel 97®. To determine the intake rate at 80% composite saturation, a line is drawn along the scatter plot parallel to the y-axis at 80% composite saturation. The intake rate is then determined from the scatter plot at the point where the line intersects the curve.

TABLE 3

| Insult # | Insult Amount (cc) | Cumulative Insult Amount (cc) | Intake Time (sec) | Intake Rate (cc/sec) | Composite Saturation (%) |
|---|---|---|---|---|---|
| 1 | 15 | 15 | 7.28 | 2.06 | 52 |
| 2 | 15 | 30 | 4.46 | 3.36 | 103 |
| 3 | 15 | 45 | 4.02 | 3.73 | 154 |

Liquid lock-up fractions are also normalized. Rather than normalizing to the composite saturation level, however, the lock-up fractions are normalized to the saturation capacity of the superabsorbent material alone. This is done to better reflect the ability of the superabsorbent material to lock-up liquid relative to the superabsorbent material total saturation capacity. Again, example normalization calculations will be done using the Sample 6. The saturation capacity of the superabsorbent material for Sample 6 is necessary for the calculations and was determined by the Centrifuge Retention Capacity Test to be 30 gram/gram. As the matrix fibers of the composite also absorb a small amount of fluid, this absorption will be taken into account in the calculations. The typical intrafiber capacities, as determined by the centrifuge retention capacity test, of the CR-1654 and CARESSA® 1300 fibers are about 1 gram liquid/gram fiber.

The lock-up fraction at 50% superabsorbent saturation is determined by plotting the lock-up fraction test data against the superabsorbent material saturation and then interpolating the value from the plot. Lock-up fraction is equal to the amount of liquid in the sample after vacuuming divided by the cumulative insult amount. The results for Sample 6 are summarized in Table 4. Superabsorbent saturation is determined according to the following formula.

$$SuperabsorbentSaturation = \frac{(A) - (B)(C)(D)}{(B)(E)(F)}$$

Where "A" is the amount of liquid in the composite after vacuum, "B" is the composite dry mass, "C" is the fiber fraction, "D" is the typical intrafiber capacity, "E" is the superabsorbent fraction, and "F" is the centrifuge retention capacity of the superabsorbent material. The fiber fraction is the total composite fiber weight divided by the total composite weight. Likewise the superabsorbent fraction is the total superabsorbent material weight divided by the total composite weight. The superabsorbent saturation values for Sample 6 are summarized in Table 4.

TABLE 4

| Insult # | Insult Amount (cc) | Cumulative Insult Amount (cc) | Amount of Liquid in Composite after Vacuum (cc) | Composite Dry Mass (g) | SAM Saturation (%) | Lock-up Fraction |
|---|---|---|---|---|---|---|
| 1 | 15 | 15 | 8.90 | 2.51 | 20 | 0.59 |
| 2 | 15 | 30 | 19.57 | 2.49 | 49 | 0.65 |
| 3 | 15 | 45 | 26.58 | 2.50 | 68 | 0.59 |

Figure 7:
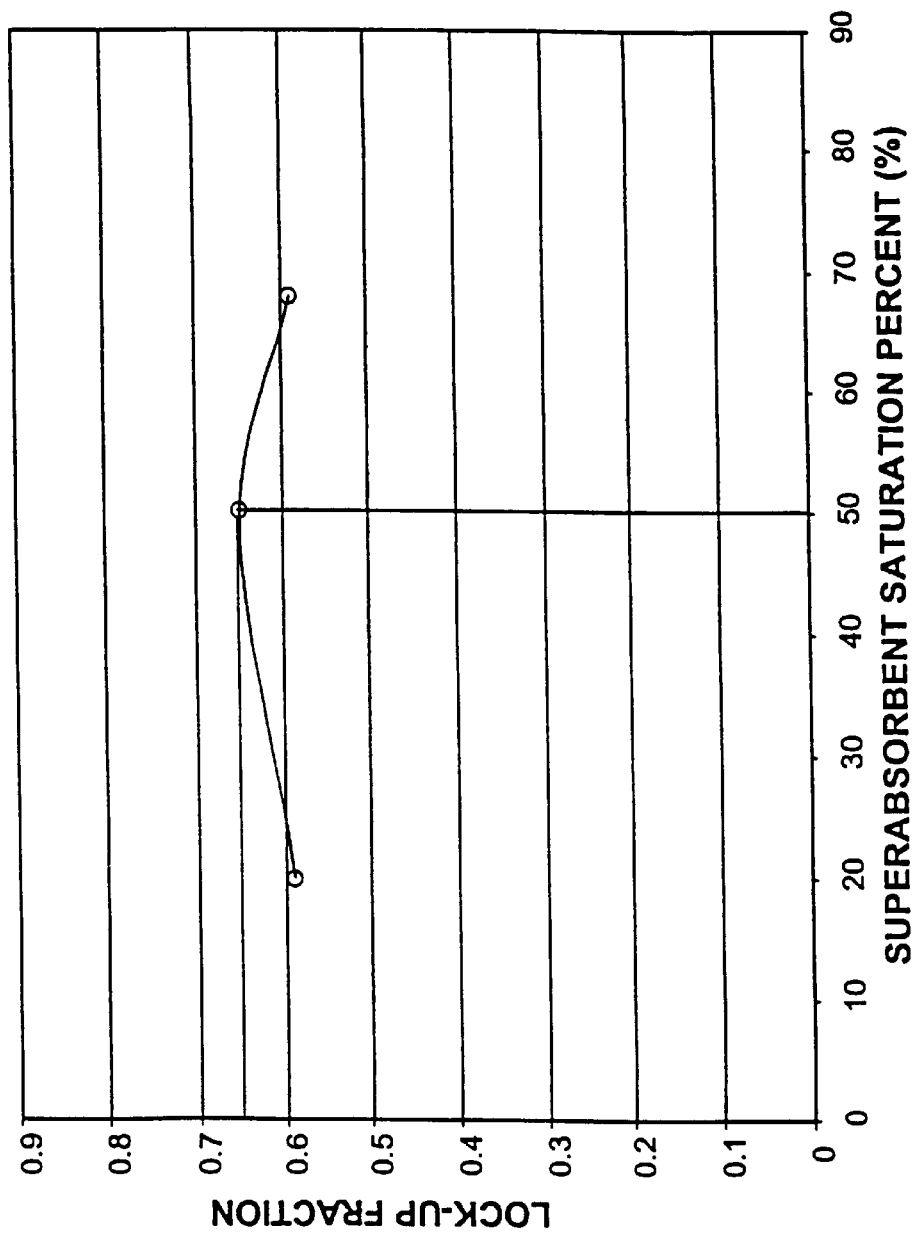
FIG. 7 is a plot of lock-up fraction against superabsorbent material saturation.

The lock-up fraction data are plotted against the respective superabsorbent material saturation percent in a scatter plot with smoothed lines. FIG. 7 shows the scatter plot for the values of Table 4 as done using the spreadsheet Microsoft Excel 97®. To determine the lock-up fraction at 50% superabsorbent saturation, a line is drawn across the scatter plot parallel to the y-axis at 50% superabsorbent saturation. The lock-up fraction is then determined from the scatter plot at the point where the line intersects the curve.

Figure 8:
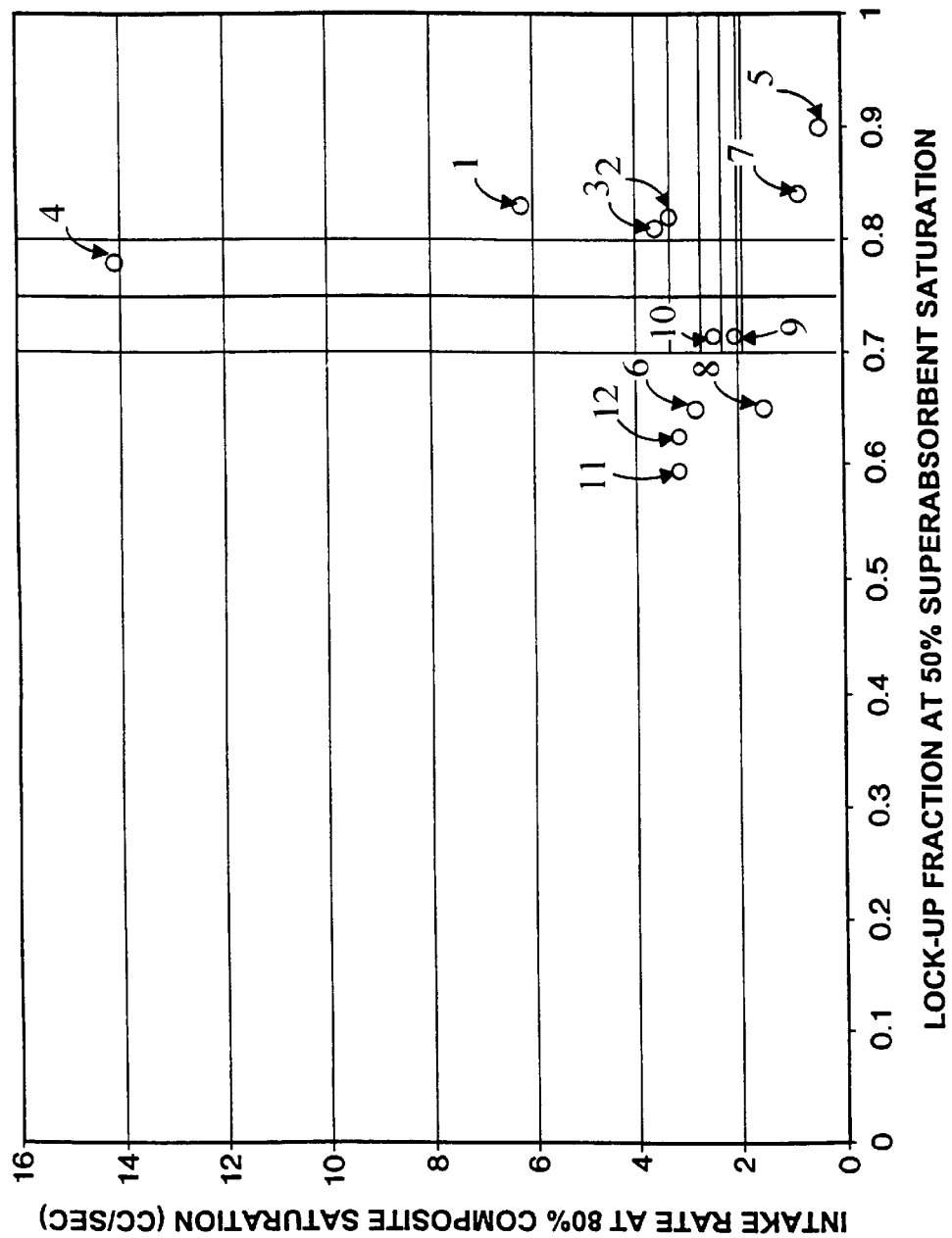
FIG. 8 is a plot of intake rate at 80% absorbent composite saturation against liquid lock-up fraction at 50% superabsorbent saturation.

Samples 1–12 were tested by the intake rate test and lock-up test. The results of testing three replicate samples are averaged and summarized in Table 5. FIG. 8 is a graph of the intake rates plotted against the lock-up fractions of the samples listed in Table 5. The freeze-dried composite Samples 1, 2, 3, and 4 and the airformed composite Samples 9 and 10 all have both the intake rate and lock-up characteristics of this invention. Freeze-dried composite sample 5, which had a 60% superabsorbent level, did not have the intake rate and lock-up characteristics of this invention. Sample 6 did have an adequate intake rate but a less than desired lock-up fraction. Samples 5 and 6 demonstrates that the intake rate and lock-up fraction of this invention are not inherent in the superabsorbent material alone but can be dependent on the structure of the composite as well as the specific superabsorbent material and fiber combination. Samples 11 and 12 also did not have the desired lock-up fraction and also demonstrate that the lock-up fraction is not dependent on the superabsorbent material alone, but on the structure of the composite as well as the specific superabsorbent material and fiber combination. Sample 7, the HUGGIES® diaper sample, exhibited an adequate liquid lock-up but a less than adequate intake rate for purposes of this invention. Sample 8, the PAMPERS® diaper sample, exhibited less than adequate intake rate and liquid lock-up fraction for the purposes of this invention. Table 5 shows the superabsorbent material of the samples as a percentage of the weight of fiber/superabsorbent material. The liquid lock-up numbers in Table 5 are at a 50% superabsorbent material saturation and the intake rates are at 80% absorbent composite saturation.

TABLE 5

| Sample | Structure | Superabsorbent Material (wt. %) | Liquid Lock-up at 50% SAM saturation | Intake Rate (cc/s) at 80% composite saturation |
|---|---|---|---|---|
| 1 | Freeze-dried composite | 50 | 0.83 | 6.2 |
| 2 | Freeze-dried composite | 50 | 0.82 | 3.3 |
| 3 | Freeze-dried composite | 50 | 0.81 | 3.6 |
| 4 | Freeze-dried composite | 30 | 0.78 | 14.1 |
| 5 | Freeze-dried composite | 60 | 0.90 | 0.40 |
| 6 | Airformed Composite | 50 | 0.65 | 2.8 |
| 7 | Diaper core | 42 | 0.84 | 0.80 |
| 8 | Diaper core | 59 | 0.65 | 1.7 |
| 9 | Airformed Composite | 50 | 0.72 | 2.1 |
| 10 | Airformed Composite | 50 | 0.72 | 2.4 |
| 11 | Airformed Composite | 50 | 0.60 | 3.3 |
| 12 | Airformed Composite | 50 | 0.64 | 3.2 |

Various conventional techniques may be employed to determine the quantitative amount of superabsorbent material within a test sample. Suitable analytical techniques include, for example, a sulfated ash measurement method, such as described in "Vogel's Textbook of Quantitative Inorganic Analysis," Fourth Edition, revised by J. Bassett, R. C. Denney, G. H. Jeffery, J. Mendham, Longman Inc., 1973, pp. 479–481, herein incorporated by reference. Another suitable technique would be an ion exchange method (e.g. sodium ion exchange), such as described in "Treatise on Analytical Chemistry," Volume 1, edited by I. M. Kolthoff and Phillip J. Elving, Interscience Publishers, Inc., 1961, pp. 345–350, herein incorporated by reference. Another suitable technique includes atomic absorption methods, such as described in "Vogel's Textbook of Quantitative Inorganic Analysis," Fourth Edition, revised by J. Bassett, R. C. Denney, G. H. Jeffery, J. Mendham, Longman Inc., 1978, pp. 310–845, herein incorporated by reference. "The Encyclopedia of Industrial Chemical Analysis," Volume 18, edited by Foster Dee Snell and Leslie S. Ettre, Interscience Publishers, Inc., 1973, at pp. 207–259, describes well known, conventional techniques for quantitatively measuring the amount of sodium within a sample, herein incorporated by reference.

The amount of superabsorbent material present in each of Samples 7 and 8 was determined by sulfated ash testing. The sulfated ash procedure converts the sodium or other cations carboxyl salt polymers, such as polyacrylate or carboxymethyl cellulose superabsorbent material, to the corresponding sulfate salt. The sulfate salt is determined gravimetrically and is calculated to the weight of the carboxyl salt polymer by applying a standard factor determined from a sample of the pure polymer. The sample is charred over a low flame to remove the bulk of the volatile matter, cooled, moistened with 1:1 sulfuric acid, the excess acid volatilized, and the ashing completed as in a regular ash determination.

The sulfated ash method can be applied to a wide range of sample sizes, including a whole diaper. Weigh a sample to the nearest 0.001 gram, into a previously ignited and tarred (to the nearest 0.1 milligram) porcelain dish or crucible. When determining the superabsorbent material content of whole diapers, as much as possible of extraneous product components (e.g. tapes, elastics) should be trimmed off first, but not so much as to lose any superabsorbent material granules. Record both the whole product weight and the trimmed weight.

Ignite the sample over a burner flame until most of the carbonaceous materials are burned off. Cool, and then moisten the entire residue with 1:1 sulfuric acid. Slowly evaporate the excess acid over a low flame so as to avoid spattering. Complete the ignition by placing the sample in a muffle, or alternatively use a forced air Meker-type burner, at 800° C.–850° C. for 60 minutes or until the ash is free of carbon. Cool in a desiccator and weigh to the nearest 0.1 milligram.

A "standard factor" is then determined for the sample. The standard factor is determined by the following formula.

$$StandardFactor(F) = \frac{(grams of oven dry polymer)}{(grams sulfated ash)(0.95)}$$

Dividing the standard factor by 0.95 takes into account the absorption of moisture that increases the weight of the sample. Depending on humidity and exposure conditions, the superabsorbent material can absorb significant levels of water (e.g. 59% at 80% RH, 100° F.). A standard 5% moisture basis is typically used in the calculation as an estimate of the additional moisture weight absorbed by the sample.

The presence of any other inorganic compound or cation, besides the superabsorbent material, will generally give a positive interference. The absence of interferences must be known and/or blank corrections must be determined if accurate results are to be obtained by this method. If samples of the material or product without added superabsorbent material are available, these can be carried through the procedure determine a correction factor. If the individual product components are available, they can likewise be analyzed and a correction factor calculated as a weighted average. The correction factor is then calculated by dividing the grams of sulfated ash by the grams of the equivalent superabsorbent free sample or components. For samples unable to have a correction factor determined by these methods, an averaged correction factor can be determined on virgin wood fluff. The typically used correction factor is 0.00513.

The calculation for the percent carboxyl salt polymer by weight of the sample is calculated by the following formula.

$$\% \ CarboxylSaltPolymer = \frac{(A - BC)(F)(100)}{(C)}$$

Where "A" is the weight of sulfated ash from the sample, "B" is the correction factor, "C" is the original weight of sample, and "F" is the standard factor. The superabsorbent material obtained by the sulphated ash testing is assumed to be at a 5% moisture basis.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An absorbent article comprising
    a liquid-permeable body-side liner;
    an absorbent composite; and
    a substantially liquid-impermeable outer cover adjacent to the absorbent composite material;
    wherein the absorbent composite has an intake rate of at least about 1.9 cubic centimeters of 0.9% by weight sodium chloride aqueous solution per second at 80% absorbent composite saturation and a liquid lock-up fraction of at least about 0.70 at 50% superabsorbent saturation determined using 0.9% by weight sodium chloride aqueous solution, the intake rate and the liquid lock-up fraction being determined by the methods set forth herein.

2. The absorbent article of claim 1, wherein the absorbent composite has an intake rate of at least about 2.3 cubic centimeters of 0.9% by weight sodium chloride aqueous solution per second at 80% absorbent composite saturation and a liquid lock-up fraction of at least about 0.75 at 50% superabsorbent material saturation determined using 0.9% by weight sodium chloride aqueous solution.

3. The absorbent article of claim 1, wherein the absorbent composite has an intake rate of at least about 2.7 cubic centimeters of 0.9% by weight sodium chloride aqueous solution per second at 80% absorbent composite saturation and a liquid lock-up fraction of at least about 0.80 at 50% superabsorbent material saturation determined using 0.9% by weight sodium chloride aqueous solution.

4. The absorbent article of claim 1, wherein the absorbent composite has an intake rate of at least about 3.3 cubic centimeters of 0.9% by weight sodium chloride aqueous solution per second at 80% absorbent composite saturation and a liquid lock-up fraction of at least about 0.80 at 50% superabsorbent material saturation determined using 0.9% by weight sodium chloride aqueous solution.

5. The absorbent article of claim 1, wherein the absorbent composite comprises a superabsorbent material in a weight amount of about 10 to 70 weight percent based on total weight of the absorbent composite.

6. The absorbent article of claim 1, wherein the absorbent composite comprises a water-insoluble fiber in a weight amount of about 30 to 90 weight percent, based on total weight of the absorbent composite.

7. The absorbent article of claim 6, wherein the water-insoluble fiber comprises at least one of a natural fiber and a synthetic fiber.

8. The absorbent article of claim 7, wherein the water-insoluble fiber comprises a fiber selected from the group consisting of wood pulp fiber, cotton linter, thermoplastic fibers, elastic fibers, and combinations thereof.

9. The absorbent article of claim 1, wherein the absorbent composite comprises a binder material in a weight amount of about 0 to 20 weight percent, based on total weight of the absorbent composite.

10. The absorbent article of claim 9, wherein the binder material is selected from the group consisting of poly (aminoamide) epichlorohydrin polymer, latex, and combinations thereof.

11. The absorbent article of claim 9, wherein the binder material comprises a water-insoluble, water-swellable polymer selected from the group consisting of sodium-polyacrylate, carboxymethyl cellulose, chitosan salt, and combinations thereof.

12. The absorbent article of claim 9, wherein the binder material comprises a thermoplastic fiber selected from the group consisting of polyethylene fibers, polypropylene fibers, polyester fibers, nylon fibers, and combinations thereof.

13. The absorbent article of claim 9, wherein the binder material is elastic.

14. The absorbent article of claim 1, wherein the absorbent composite comprises a freeze-dried fibrous composite.

15. The absorbent article of claim 1, wherein the absorbent composite comprises an airformed absorbent composite.

16. The absorbent article of claim 1, wherein the absorbent composite comprises a wetformed absorbent composite.

17. The absorbent article of claim 1, wherein the superabsorbent material comprises a material selected from the group consisting of particles, fibers, nonwoven, aggregate, printed, coated, or combinations thereof.

18. The absorbent article of claim 17, wherein the superabsorbent material comprises a material selected from the group consisting of sodium-polyacrylate, carboxymethyl cellulose, carboxymethyl polysaccharides, polyaspartic acid salt, maleic anhydride-isobutylene copolymer, chitosan salts, polyquarternary ammonium salts, polyvinyl amines, and combinations thereof.

19. The absorbent article of claim 1, wherein the absorbent article is a diaper.

20. The absorbent article of claim 1, wherein the absorbent article is a training pant.

21. The absorbent article of claim 1, wherein the absorbent article is a swim wear garment.

22. The absorbent article of claim 1, wherein the absorbent article is an adult incontinence garment.

23. The absorbent article of claim 1, wherein the absorbent article is a feminine hygiene product.

24. The absorbent article of claim 1, wherein the absorbent article is a medical absorbent product.

* * * * *